(12) United States Patent
Ito et al.

(10) Patent No.: US 10,195,595 B2
(45) Date of Patent: Feb. 5, 2019

(54) CATALYST COMPOSITION AND PROCESS FOR PRODUCING AROMATIC HYDROCARBON USING THE CATALYST COMPOSITION

(71) Applicants: Mitsui Chemicals, Inc., Minato-ku, Tokyo (JP); Agency For Science, Technology and Research, Singapore (SG)

(72) Inventors: Hideuyki Ito, Chiba (JP); Sachin Shivaji Malwadkar, Singapore (SG); Qian Zhang, Wuhan (CN); Satoru Miyazoe, Kamakura (JP)

(73) Assignees: MITSUI CHEMICALS, INC., Tokyo (JP); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 403 days.

(21) Appl. No.: 14/421,804

(22) PCT Filed: Aug. 14, 2013

(86) PCT No.: PCT/JP2013/071917
§ 371 (c)(1),
(2) Date: Feb. 13, 2015

(87) PCT Pub. No.: WO2014/027670
PCT Pub. Date: Feb. 20, 2014

(65) Prior Publication Data
US 2015/0209768 A1 Jul. 30, 2015

(30) Foreign Application Priority Data
Aug. 16, 2012 (JP) .................................. 2012-180519

(51) Int. Cl.
*B01J 29/48* (2006.01)
*C07C 2/76* (2006.01)
(Continued)

(52) U.S. Cl.
CPC .......... *B01J 29/48* (2013.01); *B01J 29/7876* (2013.01); *B01J 35/002* (2013.01); *C07C 2/76* (2013.01);
(Continued)

(58) Field of Classification Search
None
See application file for complete search history.

(56) References Cited

U.S. PATENT DOCUMENTS 8,735,310 B2  5/2014 Ma et al.
8,951,929 B2  2/2015 Liu et al.
(Continued)

FOREIGN PATENT DOCUMENTS

CN  1167653 A  12/1997
CN  1067602 C   6/2001
(Continued)

OTHER PUBLICATIONS

Examination Report for Singaporean Patent Application No. 11201501163P dated Jan. 18, 2016.
(Continued)

*Primary Examiner* — Colin W. Slifka
(74) *Attorney, Agent, or Firm* — Foley & Lardner LLP

(57) ABSTRACT

It is an object of the present invention to provide a catalyst that is excellent in stability even at a high catalyst-regeneration temperature. It is another object of the present invention to provide a process for producing an aromatic hydrocarbon from a lower hydrocarbon by using the above catalyst. The catalyst composition comprises molybdenum, a second metal that is not molybdenum, and a crystalline
(Continued)

metallosilicate, wherein the content of molybdenum is 1 to 20% by weight in terms of a molybdenum atom, and the content of the second metal is 2 to 20% by weight in terms of a metal atom.

11 Claims, 4 Drawing Sheets

(51) Int. Cl.
*B01J 29/78* (2006.01)
*B01J 35/00* (2006.01)
*C10G 45/68* (2006.01)
*B01J 29/90* (2006.01)

(52) U.S. Cl.
CPC .............. *C10G 45/68* (2013.01); *B01J 29/90* (2013.01); *C07C 2529/48* (2013.01); *C10G 2400/30* (2013.01); *Y02P 20/52* (2015.11); *Y02P 20/582* (2015.11); *Y02P 20/584* (2015.11); *Y02P 20/588* (2015.11)

(56) References Cited

U.S. PATENT DOCUMENTS

| | | |
|---|---|---|
| 2010/0137125 A1 | 6/2010 | Ma et al. |
| 2010/0185034 A1 | 7/2010 | Nishimura et al. |
| 2010/0234658 A1 | 9/2010 | Karim et al. |
| 2010/0285948 A1 | 11/2010 | Liu et al. |
| 2010/0312029 A1 | 12/2010 | Gulotty et al. |
| 2012/0142986 A1 | 6/2012 | Okabe et al. |

FOREIGN PATENT DOCUMENTS

| | | |
|---|---|---|
| JP | 10-272366 A | 10/1998 |
| JP | H10-272366 A | 10/1998 |
| JP | 2005-230644 A | 9/2005 |
| JP | 2008-266245 A | 11/2008 |
| JP | 2008-302291 A | 12/2008 |
| JP | 2010-535623 A | 11/2010 |
| JP | 2011-509823 A | 3/2011 |
| WO | WO-2009/020045 A1 | 2/2009 |
| WO | WO-2010/069582 A1 | 6/2010 |
| WO | WO-2011/018966 A1 | 2/2011 |

OTHER PUBLICATIONS

Izhar et al., "Cobalt molybdenum carbides: Surface properties and reactivity for methane decomposition", ScienceDirect, Applied Catalysis A: General, Issn 0926-860X, vol. 317, Issue 1, Jan. 2007, pp. 82-90.

Kuang et al., "Catalytic properties of ultrafine molybdenum-cerium oxide particles prepared by the sol-gel method", Catalysis Letters, vol. 50, No. 1.2, pp. 31-35, Feb. 1998.

Li et al., "Thermal and hydrothermal stabilities of the alkali-treated HZSM-5 zeolites", ScienceDirect, Journal of Natural Gas Chemistry, vol. 17, No. 1, pp. 69-74, Mar. 2008.

Liu et al., "Methane dehydroaromatization over Mo/HZSM-5 catalysts: The reactivity of $MoC_x$ species formed from $MoO_x$ associated and non-associated with Bronsted acid sites", Science Direct, Applied Catalysis A;General vol. 295, pp. 79-88, Oct. 2005.

Liu et al., "Methane dehydrogenation and aromatization in the absence of oxygen on Mo/HZSM-5: A study on the interaction between Mo Species and HZSM-5 by using $^{27}Al$ and $^{29}Si$ MAS NMR", Journal of Molecular Catalysis A:Chemical, Issn 1381-1169, vol. 120, No. 1-3, Jun. 1997, pp. 257-265.

Liu et al., "Methane Dehydrogeneration and Aromatization over Mo/HZSM-5: In Situ FT-IR Characterization of its Acidity and the Interaction between Mo Species and HZSM-5", Journal of Catalysis, vol. 185, No. 2, Jul. 1999.

Ma et al., "Efficient regeneration of Mo/HZSM-5 catalyst by using air with NO in methane dehydro-aromatization reaction", Applied Catalysis A: General, Issn 0926-860X, vol. 275, Issues 1-2, Nov. 2004, pp. 183-187.

Zhang et al., "Methane Dehydro-aromatization over Mo/HZSM-5 in the Absence of Oxygen: A Multinuclear Solid-State NMR Study of the Interaction between Supported Mo Species and HZSM-5 Zeolite with Difference Crystal Sizes", Journal of Catalysis, Issn 0021-9571, vol. 188, No. 2, Dec. 1999, pp. 393-402.

Skutil et al., "Some technological aspects of methane aromatization (direct and via oxidative coupling)", Fuel Processing Technology, vol. 87, No. 6, pp. 511-521, Jun. 2006.

Wang et al., "Dehydrogenation and aromatization of methane under non-oxidizing conditions", Catalysis Letters 21, vol. 21, pp. 35-41, Jan. 1993.

International Search Report issued in PCT/JP2013/071917 dated Nov. 12, 2013.

Dong et al., "Studies on Mo/HZSM-5 Complex Catalyst for Methane Aromatization," Journal of Natural Gas Chemistry, vol. 13, 2004, pp. 36-40.

[Fig. 1]
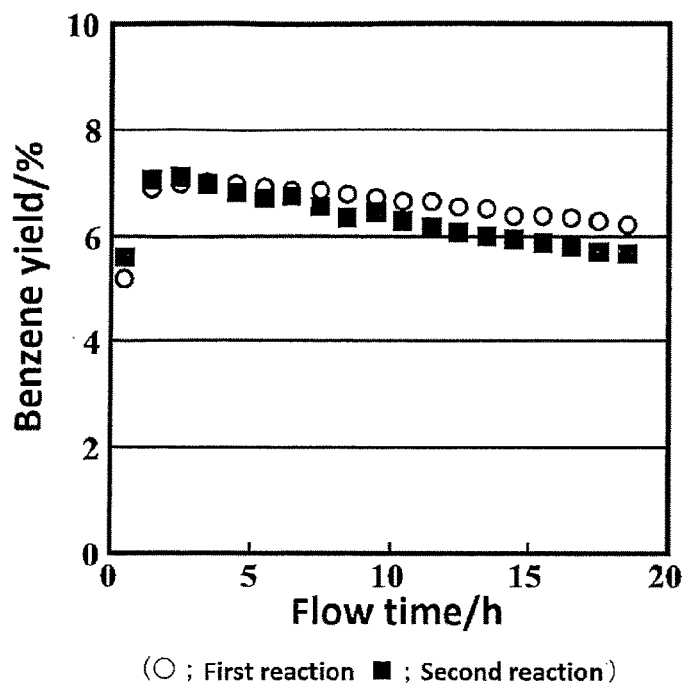
(○ ; First reaction  ■ ; Second reaction)
[Fig. 2]
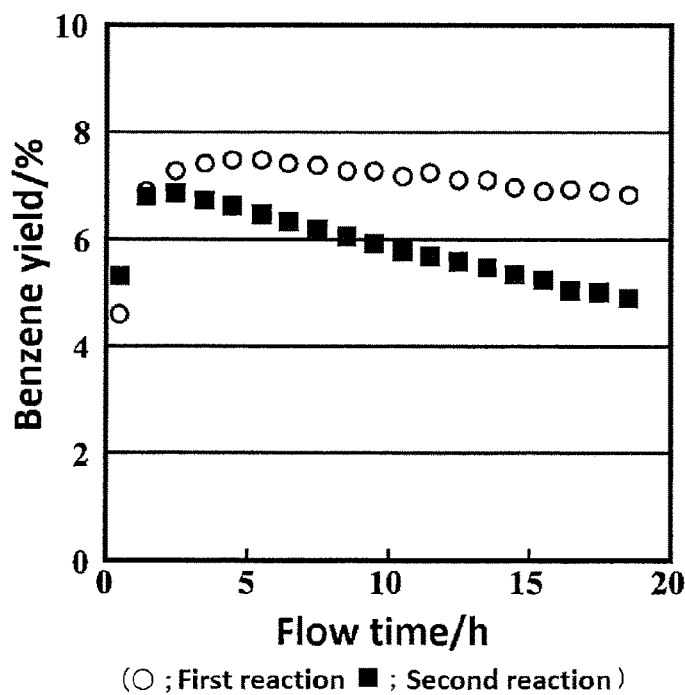
(○ ; First reaction  ■ ; Second reaction)

[Fig. 3]
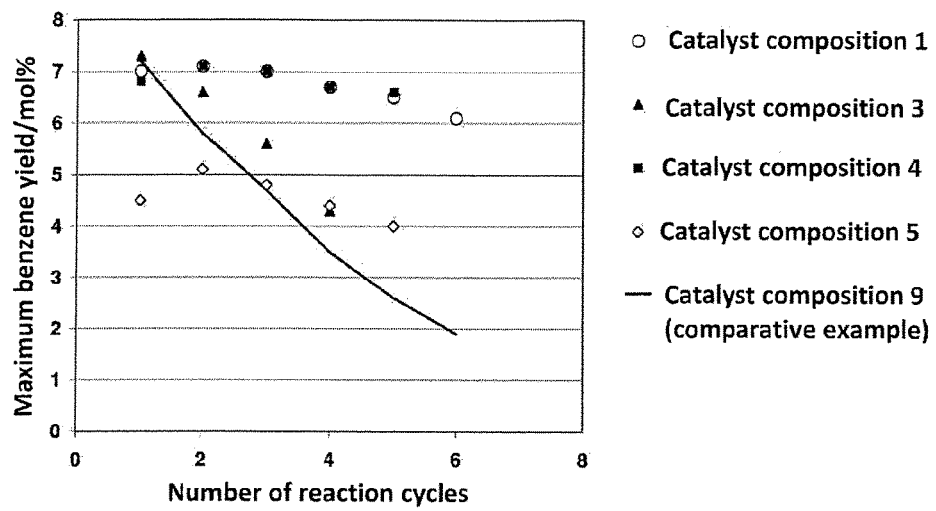
[Fig. 4]
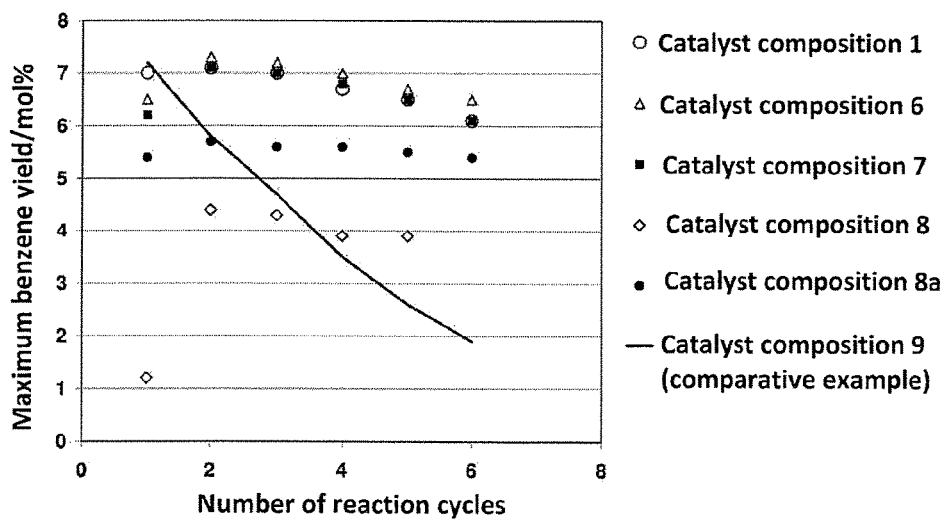

[Fig. 5a]
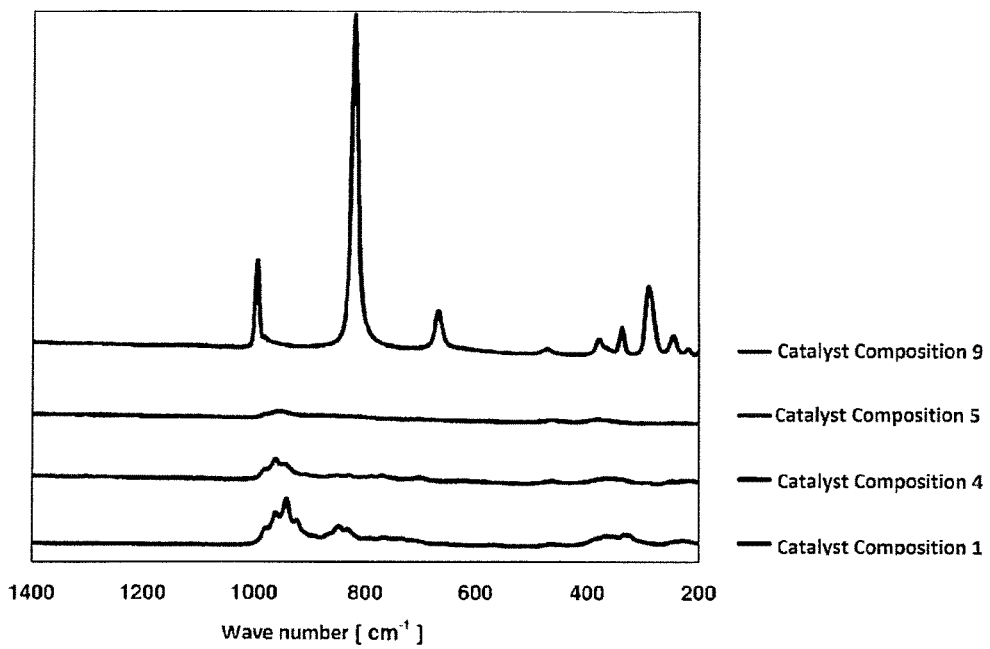
[Fig. 5b]
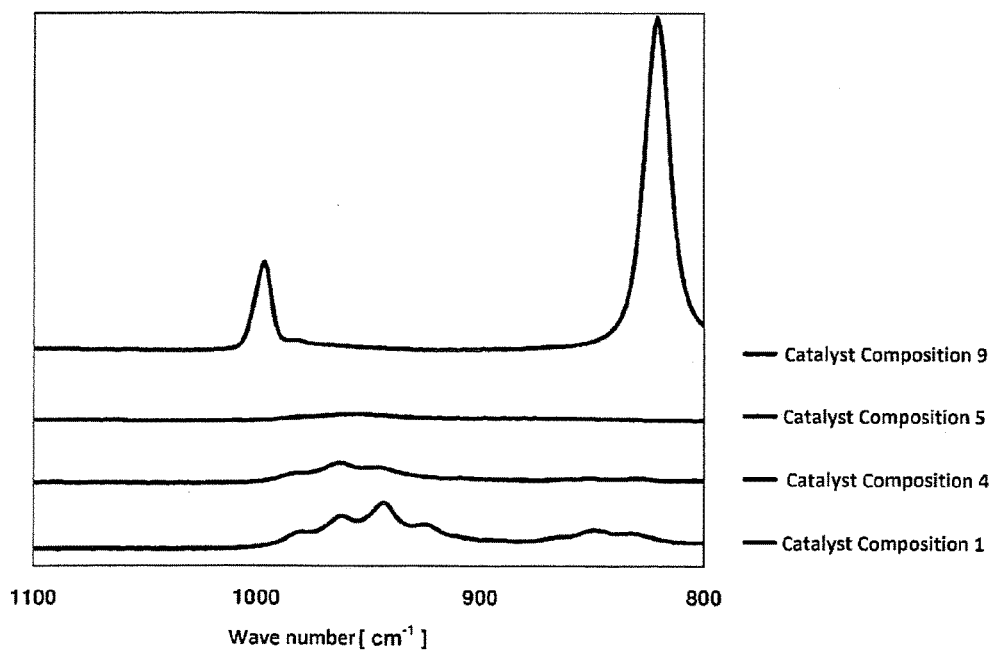

[Fig. 5c]
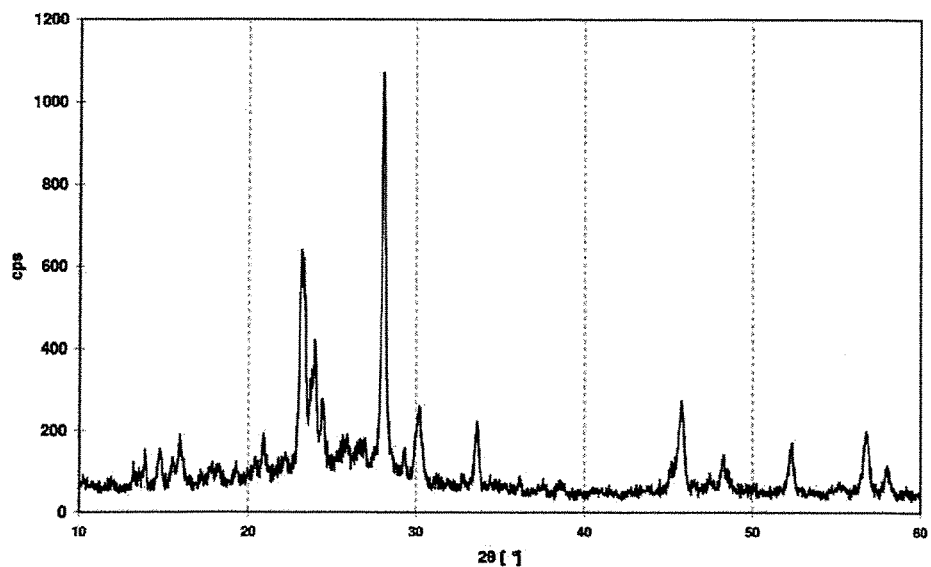
[Fig. 5d]
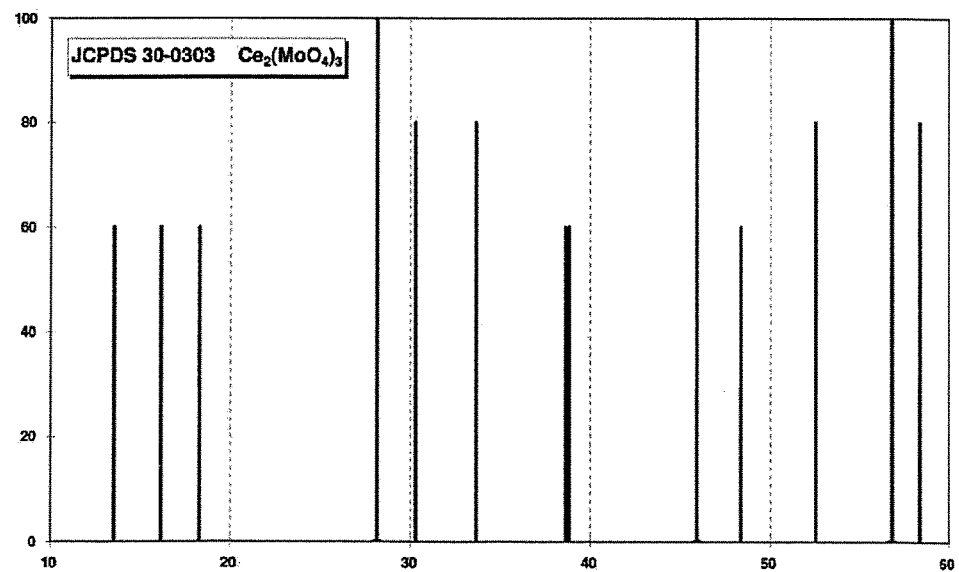

CATALYST COMPOSITION AND PROCESS FOR PRODUCING AROMATIC HYDROCARBON USING THE CATALYST COMPOSITION

CROSS REFERENCE TO RELATED APPLICATIONS

This application is the National Phase of PCT/JP2013/071917, filed Aug. 14, 2013, which claims priority to Japanese Application No. 2012-180519, filed Aug. 16, 2012.

TECHNICAL FIELD

The present invention relates to a catalyst composition comprising molybdenum, a second metal that is not molybdenum, and a crystalline metallosilicate. Further, the present invention relates to a process for efficiently producing an aromatic hydrocarbon useful as a chemical industrial raw material from a lower hydrocarbon such as methane in the presence of the catalyst composition.

BACKGROUND ART

Most of aromatic hydrocarbons which are useful as chemical industrial raw materials, such as benzene, toluene and xylene, have been produced in the past as by-products in gasoline production in the petroleum refining industry or ethylene production in the petrochemical industry. In either case, such aromatic hydrocarbons are not the desired products, and therefore, yields on the basis of crude oil that is a starting raw material are not high. Further, the production is controlled by the supply-demand situation on the side of each desired product. As a production process for an aromatic hydrocarbon that is a desired product, a process using a light component derived from crude oil has been developed, and a part of it has been commercialized, but the production thereof still remains small.

On the other hand, the amounts of natural gas reserves in the whole world are said to be about 6600 TCF (1 TCF is an abbreviation of one trillion cubic feet), but most of them have not been used effectively. The technique to produce an aromatic hydrocarbon from methane that is a main component of natural gas is a method capable of not only adding a high value to abundant natural gas but also converting raw material sources of aromatic hydrocarbons that are important chemical industrial raw materials from crude oil resources into non-crude oil resources, and practical use thereof has been desired.

As a catalyst which is widely known to exhibit excellent performance as a catalyst capable of directly producing an aromatic hydrocarbon using methane as a raw material and which has been best studied, a zeolite-supported molybdenum catalyst (non patent literature 1) found by L. Wang, et al. in 1993 can be mentioned. In techniques having been disclosed so far, crystalline metallosilicate having a transition metal supported thereon, particularly, MFI-type zeolite or MWW-type zeolite having molybdenum, tungsten or rhenium supported thereon, is widely known as a catalyst capable of directly producing an aromatic hydrocarbon from methane efficiently.

As the temperature becomes higher in the reaction to produce an aromatic hydrocarbon from methane, the reaction becomes more advantageous because of thermodynamic equilibrium. For example, in the reaction to produce benzene from methane, the equilibrium conversion in the reaction at 700° C. is about 11%, while the equilibrium conversion in the reaction at 800° C. is estimated to be about 20%. In order to efficiently produce an aromatic hydrocarbon, therefore, the reaction temperature of this reaction system is limited to 600° C. or higher, preferably 700° C. or higher.

Moreover, it is known that a carbonaceous substance is deposited on the above catalyst during the reaction and causes deactivation of the catalyst. The carbonaceous substance deposited on the catalyst is burned off in a high-temperature oxygen-containing atmosphere. Then, in order to use the catalyst for a long period of time, a method of alternately repeating a reaction step and a catalyst regeneration step of heat-treating the catalyst in an oxygen-containing atmosphere has been proposed.

However, if the reaction step and the regeneration step are alternately repeated actually, the catalyst is gradually deteriorated, and production of an aromatic compound cannot be carried out over a long period of time, so that this method has not been put to practical use yet (e.g., non patent literature 2).

The cause of deterioration of the catalyst has not been clarified sufficiently, but some estimated mechanisms described below have been proposed. That is to say, a theory that a part of a crystalline structure of a crystalline metallosilicate is thermally collapsed under the high-temperature conditions to thereby exhibit lower catalytic performance (non patent literature 3), a theory that the melting point of molybdenum oxide is as low as 795° C., and therefore, if catalyst regeneration treatment in an oxygen-containing atmosphere is carried out at a high temperature, decrease in the number of active sites due to vaporization or sintering is brought about (non patent literature 4), a theory that at a high temperature, molybdenum partially reacts with an aluminum atom in a metallosilicate crystal lattice to form an inert $Al_2(MoO_4)_3$ species, and this leads to decrease in the number of active sites (non patent literatures 5, 6 and 7), etc. can be mentioned.

There is a possibility that the catalyst deterioration is brought about by exposure of the catalyst containing molybdenum oxide to a high temperature whatever the deterioration mechanism may be, and therefore, it is thought that if the treatment temperature can be lowered in the catalyst regeneration step, the deterioration can be inhibited. However, if the treatment temperature in the catalyst regeneration step is low, removal of the deposited carbonaceous substance by burning becomes insufficient, and the catalytic activity cannot be completely recovered. On that account, the deposited carbonaceous substance is removed with inhibiting catalyst deterioration in the catalyst regeneration step, and therefore, the catalyst regeneration temperature is limited. For example, in a patent literature 1, a temperature of 400 to 500° C. is given as an example of the catalyst regeneration temperature.

In order to efficiently remove the carbonaceous substance in the catalyst regeneration step, a method of combining a carbonaceous substance removing treatment using a reducing gas such as hydrogen with a carbonaceous substance removing treatment using an oxidizing gas has been proposed in, for example, a patent literature 3. In a non patent literature 8, in order to reduce catalyst deterioration in the regeneration step for a catalyst, an attempt to lower the regeneration temperature has been made by adding a small amount of nitrogen monoxide to air that is a regeneration gas. In the non patent literature 8, it is described that as compared with a case where a catalyst is regenerated in air at 550° C., the regeneration temperature can be lowered down to 450° C. in the case where a mixed gas of air and nitrogen monoxide is used, and as a result, the number of regeneration times of the catalyst can be increased. However, it is said that even if a regeneration method using air to which a small amount of nitrogen monoxide has been added is used, the catalytic activity is gradually lost by repeating the reaction step and the regeneration step, and therefore, a more efficient catalyst regeneration method has been desired by the industry.

From the above, improvement in thermal stability (durability) of a catalyst is an industrial problem from the viewpoint of the catalyst life. With regard to a catalyst for producing an aromatic hydrocarbon from a hydrocarbon containing methane as a main component, it has been found in, for example, a patent literature 2 that thermal stability of a crystalline metallosilicate can be improved by combining inhibition of elimination of a metal from the crystalline metallosilicate with a surface modification treatment using a transition metal or an alkaline earth metal. However, a specific technique to inhibit lowering of activity accompanying repetition of the reaction step and the regeneration step has not been disclosed at all.

Moreover, several techniques to improve catalytic performance by adding a second metal component have been disclosed so far. For example, in a patent literature 4, performance of a catalyst constituted of at least one metal selected from Mo, Ce and Cs, La and zeolite is disclosed. In a patent literature 5, performance of a catalyst constituted of Mo, a transition metal (at least one metal selected from Ti, Zr, Cr, W, Co, Ru and Ni), a rare earth metal (at least one metal selected from La, Ce, Pr, Nd and Sm) and zeolite is disclosed. In a patent literature 6, a preparation process for a methane dehydroaromatization catalyst, which is characterized by comprising a step of heating a catalyst precursor containing molybdenum and aluminosilicate in the presence of a treating gas containing propane in order to improve efficiency of the methane dehydroaromatization catalyst, is disclosed, and it is described that the catalyst precursor preferably contains a metal (Ga, Zn, Nb, Zr, La, Co, Fe, Ce, Ag, Y, V, Sr, W, Yb, Sm, Ni, Ru, Rh, Pt, Cu, Au, Al, Ti, Pb, Re, Ir, Si, Sn and Pd) as a promoter. That is to say, this process relates to an invention in which a catalyst is changed to be in such a state that it can maintain a high yield for a long time by a technique of, for example, preliminarily contacting the catalyst with a certain kind of a gas prior to the reaction, but description of heat resistance (thermal stability) of a molybdenum-based supported catalyst, namely, description of a method for efficiently regenerating a catalyst whose activity has been lowered, by removing carbon produced on the catalyst as a by-product at a high temperature during aromatization reaction of a hydrocarbon such as methane, is not observed.

Further, it is disclosed that the chemical properties of Mo are changed by the addition of a second metal (e.g., non patent literature 9, non patent literature 10), but it cannot be said yet that the stability of catalytic activity is satisfactory.

CITATION LIST

Patent Literature

Patent literature 1: Japanese Patent Laid-Open Publication No. 2008-302291
Patent literature 2: WO2011/018966
Patent literature 3: Japanese Patent Laid-Open Publication No. 2008-266245
Patent literature 4: Japanese Patent Laid-Open Publication No. 2010-535623
Patent literature 5: CN1067602(C)
Patent literature 6: Japanese Translation of PCT International Application Publication No. 2011-509823

Non Patent Literature

Non patent literature 1: Catalysis Letters, 1993, Vol. 21, p. 35
Non patent literature 2: Fuel Processing Technology, 2006, Vol. 87, p. 511
Non patent literature 3: Journal of Natural Gas Chemistry, 2008, Vol. 17, p. 69
Non patent literature 4: Applied Catalysis A: General, 2005, Vol. 295, p. 79
Non patent literature 5: Journal of Catalysis, 1999, Vol. 185, p. 386
Non patent literature 6: Journal of Molecular Catalysis A: Chemical, 1997, Vol. 120, p. 257
Non patent literature 7: Journal of Catalysis, 1999, Vol. 188, p. 393
Non patent literature 8: Applied Catalysis A: General, 2004, Vol. 275, p. 183
Non patent literature 9: Applied Catalysis A: General, 2007, Vol. 317, p. 82
Non patent literature 10: Catalysis Letter, 1998, Vol. 50, p. 31

SUMMARY OF INVENTION

Technical Problem

It is an object of the present invention to provide a catalyst composition which is excellent in stability under the conditions of catalyst regeneration wherein the catalyst composition is heated in an oxygen-containing atmosphere. It is another object of the present invention to provide a process for producing an aromatic hydrocarbon from a lower hydrocarbon, in which deterioration of performance of the catalyst composition is inhibited over a long period of time.

Solution to Problem

The present inventors have presumed that if a zeolite-supported molybdenum catalyst on which a carbonaceous substance has been deposited is heat-treated in an oxygen-containing atmosphere in order to regenerate the catalyst, migration property of the molybdenum species on the catalyst surface is enhanced to increase frequency of reaction of molybdenum with aluminum in a zeolite framework, and as a result, formation of $Al_2(MoO_4)_3$ species, destruction of a crystalline structure of zeolite and rupture of acidic active sites of zeolite are brought about, and a cause-effect relationship among a series of these phenomena is a cause of deterioration of the zeolite-supported molybdenum catalyst. On the basis of this presumption, the present inventors have earnestly studied a method for lowering migration property of the molybdenum species in the regeneration step, and as a result, they have got an idea that by incorporating, as a second metal, a metal oxide capable of forming a composite oxide together with molybdenum oxide to a zeolite-supported molybdenum catalyst, migration property of the molybdenum species is lowered. As a result of further studies, the present inventors have found that by incorporating a specific second metal in a molybdenum-containing catalyst, heat resistance (thermal stability) of a catalyst composition is improved, and catalyst deterioration in the catalyst regeneration step is inhibited. Thus, the present invention has been accomplished.

That is to say, the catalyst composition of the present invention is as follows.

[1] A catalyst composition for producing an aromatic hydrocarbon by contacting at least one hydrocarbon with the catalyst composition, comprising molybdenum, a second metal that is not molybdenum, and a crystalline metallosilicate, wherein the content of molybdenum is 1 to 20% by weight in terms of a molybdenum atom and the content of the second metal is 2 to 20% by weight in terms of a metal atom.

[2] The catalyst composition as stated in the above [1], wherein the second metal is at least one metal selected from the group consisting of Sc, Y and lanthanoids (La, Ce, Pr, Nd, Pm, Sm, Gd, Tb, Dy, Ho, Er, Tm, Yb or Lu).

[3] The catalyst composition as stated in the above [1] or [2], wherein a relative weight reduction ratio (C) defined by the following formula is 60% or less;

$$C=100A/B;$$

wherein,

A is a weight variation in terms of %, which is defined as a deviation in weight at a temperature of 900° C. based on a weight measured at a temperature of 650° C. wherein the measurement is conducted by heating the catalyst composition with a differential thermogravimetric analyzer at a temperature increase rate of 5° C. per minute from a room temperature to 900° C. in air atmosphere, wherein the weight of the catalyst composition is normalized such that the weight of the catalyst composition at 650° C. is 100%, B is molybdenum oxide content in terms of wt % to the total wt % of a catalyst composition (100 wt %) in which both of the molybdenum and the second metal are present in the form of oxides.

[4] The catalyst composition as stated in the above [1] or [2], wherein in an x-ray diffraction analysis of said catalyst composition, at least one peak attributed to a composite oxide phase of molybdenum and the second metal, which is different from a peak attributed to a single phase of each of molybdenum oxide and the second metal oxide, is observed.

[5] The catalyst composition as stated in the above [1] or [2], wherein in a Raman spectroanalysis the ratio (Y/X) of a maximum peak strength of the spectrum in the range of 980 to 1020 $cm^{-1}$ (Y) to a maximum peak strength of the spectrum in the range of 900 to 970 $cm^{-1}$ (X) is 0.8 or lower.

[6] The catalyst composition as stated in any one of the above [1] to [5], wherein the second metal is at least one metal selected from the group consisting of Ce, Pr, Tb and Y.

[7] The catalyst composition as stated in any one of the above [1] to [6], wherein the ratio (y/x) of the content (y mol) of the second metal atom to the content (x mol) of the molybdenum atom is 0.2 to 15.

[8] The catalyst composition as stated in any one of the above [1] to [7], wherein the second metal is at least one metal selected from the group consisting of Ce, Pr, Tb and Y, and the ratio (y/x) of the content (y mol) of the second metal atom to the content (x mol) of the molybdenum atom is 0.2 to 15.

[9] The catalyst composition as stated in any one of the above [1] to [8], wherein the crystalline metallosilicate has a pore having a diameter of 4 to 9 Å.

[10] The catalyst composition as stated in the above [9], wherein the crystalline metallosilicate has a MFI-type or a MWW-type crystalline structure.

[11] The catalyst composition as stated in the above [10], wherein the crystalline metallosilicate is aluminosilicate.

[12] A process for producing an aromatic hydrocarbon comprising a step of contacting at least one hydrocarbon with the catalyst composition as stated in any one of the above [1] to [11].

[13] The process for producing an aromatic hydrocarbon as stated in the above [12], wherein the hydrocarbon is an aliphatic hydrocarbon having 1 to 6 carbon atoms.

[14] The process for producing an aromatic hydrocarbon as stated in the above [12] or [13], which further comprises a regeneration step of heating the catalyst under an oxygen-containing atmosphere to a temperature of 400° C. or higher.

Advantageous Effects of Invention

The catalyst composition of the present invention exerts an effect that it has high stability even when it is subjected to a regeneration treatment under the high-temperature conditions and it is hardly deteriorated in performance. Further, even if a regeneration step is repeated in the process for producing an aromatic hydrocarbon from a lower hydrocarbon, deterioration of catalytic performance can be inhibited over a long period of type by using the catalyst composition of the present invention. Furthermore, the regeneration time can be shortened by treating the catalyst at a high temperature, and therefore, economical efficiency of the production process can be enhanced.

BRIEF DESCRIPTION OF DRAWINGS

FIG. 1 is view showing a change of a benzene yield with time in each reaction in the case where a first aromatization reaction of methane (700° C., normal pressure) is carried out using a catalyst composition 1, thereafter a catalyst regeneration step (in air, 600° C., 1 hour) is carried out, and then a second aromatization reaction of methane is carried out.

FIG. 2 is view showing a change of a benzene yield with time in each reaction in the case where a first aromatization reaction of methane (700° C., normal pressure) is carried out using a catalyst composition 9, thereafter a catalyst regeneration step (in air, 600° C., 1 hour) is carried out, and then a second aromatization reaction of methane is carried out.

FIG. 3 is a view indicating that catalyst deterioration of the catalyst composition of the present invention due to repetition of a reaction step and a catalyst regeneration step has been inhibited.

FIG. 4 is a view indicating that catalyst deterioration of the catalyst composition of the present invention due to repetition of a reaction step and a catalyst regeneration step has been inhibited.

FIG. 5a is a view in which measurement results of Raman spectroscopy of catalyst compositions 1, 4, 5 and 9 are multiple-plotted.

FIG. 5b is an enlarged view of the 800 to 1100 $cm^{-1}$ portion in FIG. 5a.

FIG. 5c shows results of an X-ray diffraction analysis of a catalyst composition 1 after the catalyst composition 1 was used in Example 1 and subjected to the sixth regeneration treatment.

FIG. 5d is a graph showing diffraction peak positions and strength ratios of JCPDS30-0303.

DESCRIPTION OF EMBODIMENTS

The catalyst composition of the present invention and the process for producing an aromatic hydrocarbon using the catalyst composition are specifically described hereinafter. The embodiments given here are those specifically explaining the present invention in order that the idea of the present invention might be better understood, and the present invention is in no way limited to them.

[Catalyst Composition]

The catalyst composition of the present invention comprises molybdenum, a second metal that is not molybdenum (sometimes called a "second metal" for short in the following description) and a crystalline metallosilicate. Molybdenum is preferably contained in an amount of 1 to 20% by weight, more preferably 2 to 15% by weight, in terms of a metal atom. The term "% by weight" occupied by the molybdenum atom in the catalyst composition means a value based on the total weight of the molybdenum atom, the second metal atom and the crystalline metallosilicate. This is a value independent of a weight variation of oxygen atom or carbon atom attributable to a change of the state of molybdenum or the second metal contained and addition of a third component such as a binder. Also with regard to the content of the second metal, the same definition as above is used.

The molybdenum raw material for preparing the catalyst composition is not specifically limited and all available molybdenum compounds and metallic molybdenum can be used. Examples of molybdenum raw materials that are relatively easily obtainable include molybdenum oxide, molybdenum carbide, molybdenum sulfide, ammonium heptamolybdate, sodium molybdate, ammonium paramolybdate, 12-molybdophosphoric acid and 12-molybdosilicic acid.

The second metal is at least one metal selected from a group of metals, such as alkaline metals (Li, Na, K, Rb, Cs, Sc), alkaline earth metals (Mg, Ca, Sr, Ba) and rare earth metals (Y, La, Ce, Pr, Nd, Pm, Sm, Eu, Gd, Tb, Dy, Ho, Er, Tm, Yb, Lu). Preferable are rare earth metals, and more preferable is at least one metal selected from Ce, Pr and Tb. The second metal is preferably contained in the catalyst composition in an amount of 2% by weight to 20% by weight, more preferably more than 2% by weight but not more than 20% by weight, particularly preferably not less than 5% by weight but not more than 20% by weight, in terms of a metal atom.

In the catalyst composition of the present invention, the ratio of the content (y mol) of the second metal atom to the content (x mol) of the molybdenum atom is one of its characteristics, and the value of y/x is usually 0.1 to 15, preferably 0.2 to 10, more preferably 0.4 to 5.

Examples of the crystalline metallosilicates to constitute the catalyst composition of the present invention include zeolite, aluminosilicate, gallosilicate, galloaluminosilicate, borosilicate and phosphoaluminosilicate. The pore diameters of these metallosilicates are preferably 4 to 9 Å, more preferably 4 to 6 Å.

Of the above crystalline metallosilicates, preferable are crystalline metallosilicates having structures of FAU-type, LTL-type, BEA-type, MOR-type, FER-type, MFI-type, MTW-type, MEL-type, CHA-type, MTT-type, DON-type, TON-type, MWW-type, NES-type, MFS-type, STF-type, STT-type, SFG-type, KFI-type, IWR-type, ITH-type, IWW-type, etc., and of these, zeolite is particularly preferable. Still more preferable is MFI-type zeolite such as ZSM-5-type zeolite or MWW-type zeolite such as MCM-22-type zeolite.

When the above zeolite is used, it can have a silica-alumina ratio of such an arbitrary range that the stability of the zeolite structure is not impaired. The silica/alumina ratio is preferably smaller, and is usually 100 or less, preferably 55 or less, more preferably 45 or less, still more preferably 35 or less, particularly preferably 30 or less. Although the lower limit of the silica/alumina ratio is not specifically restricted, it is usually about 25. In this case, zeolite synthesized in such a manner that the silica/alumina ratio becomes the above value can be also used, or before or after introduction of molybdenum and the second metal, the silica/alumina ratio can be controlled by carrying out a publicly known method such as dealumination prior to use.

One of the characteristics of the catalyst composition of the present invention is low migration property of a molybdenum species in the regeneration step. After the catalyst composition is heat-treated in an oxygen-containing atmosphere, a composite oxide of molybdenum and the second metal has been formed in some cases. Migration property of the molybdenum species can be evaluated using, as an indication, "weight reduction due to sublimation of molybdenum oxide" observed when molybdenum oxide is heat-treated by increase in temperature in air atmosphere. That is to say, the ratio of a measured weight variation to a content (wt %) of molybdenum oxide in the catalyst composition is calculated as a relative weight reduction ratio (%).

Specifically, in the first place, using a differential thermogravimetric analyzer, the measurement is conducted by heating the catalyst composition from room temperature up to 900° C. in an air atmosphere under the conditions of a temperature increase rate of 5° C./min. In this measurement, the weight of the catalyst composition is normalized such that the weight of the catalyst composition at 650° C. is 100%, and a deviation in weight (A wt %) at a temperature of 900° C. is determined. Next, the content (B wt %) of molybdenum oxide to the total weight (100 wt %) of a catalyst composition in which both of the molybdenum and the second metal are present in the form of oxides is determined. Finally, using the A wt % and the B wt % determined above, a relative weight reduction ratio (C) is calculated from the following formula.

Relative weight reduction ratio $C(\%)=100A/B$

For example, when a HZSM-5 zeolite catalyst on which 12 wt % of molybdenum and 10 wt % of cerium have been supported exhibits a weight reduction of 0.4 wt % between 650° C. and 900° C. in the measurement using a differential thermogravimetric analyzer, the relative weight reduction ratio is determined as follows. The Mo/Ce/zeolite weight ratio is 12/10/78, and when this is converted to a ratio in the case where both of molybdenum and cerium are in the form of oxides, the $MoO_3/CeO_2$/zeolite weight ratio is determined as 18.00/12.28/78, namely, 16.63/11.34/72.03, so that the content (wt %) of the molybdenum oxide is 16.63%. Consequently, the relative weight reduction ratio in this case is calculated to be 100×(0.4)/16.32=2.4%.

The relative weight reduction ratio (C) of the catalyst composition of the present invention is 60% or less, preferably 30% or less, more preferably 10% or less.

One of methods to detect formation of a composite oxide of molybdenum and the second metal in the catalyst composition of the present invention is XRD measurement, and powder X-ray diffraction measurement using a powder of a catalyst composition is commonly used. Peak positions of crystalline phases of composite oxides of molybdenum and a second metal are different in every composite oxide, and therefore, it is difficult to define, as a specific diffraction angle, a peak position of a composite oxide phase detected in the catalyst composition of the present invention. When crystalline structure data of a publicly known molybdenum-containing composite oxide phase are compared with the measured data, at least one peak corresponding to the composite oxide phase is exhibited, whereby formation of a molybdenum-containing composite oxide can be grasped. Examples of crystalline structures of publicly known molybdenum-containing composite oxide phases include JCPDS number (Joint Committee on Powder Diffraction Standards) 33-0330, 30-0303, 33-0936, 31-0330, 35-1477, 28-0861, 25-0934 and 33-0936.

Another method to detect formation of the composite oxide is Raman spectroscopy. It is known that one of absorption peaks derived from MoO3 appears in the range of 980 to 1020 $cm^{-1}$, while a molybdenum-containing composite oxide exhibits an absorption peak in the range of 900 to 970 $cm^{-1}$. Then, if a maximum peak strength in the range of 900 to 970 $cm^{-1}$ is represented by X and a maximum peak strength in the range of 980 to 1020 $cm^{-1}$ is represented by Y and if a ratio of Y/X is small, it can be considered that a metal oxide phase containing molybdenum and the second metal has been formed. The Y/X ratio of the catalyst composition of the present invention is 0.8 or less, preferably 0.5 or less, more preferably 0.2 or less. A catalyst composition exhibiting no peak in the range of 980 to 1020 $cm^{-1}$ (that is, Y=0) is particularly preferable.

The production process for the catalyst composition of the present invention is not specifically restricted provided that it is a production process for a heterogeneous catalyst. For the production, any of publicly known methods, such as an evaporation drying method using a metal salt, an incipient wetness method, a pore filling method and an ion exchange method, may be used.

When the catalyst composition of the present invention is prepared by an impregnation supporting method, there is no limitation on the order of supporting two kinds of the metal components and the method for supporting them, and the metal components can be supported on a carrier simultaneously or successively by an arbitrary method.

After the metal components are supported on the catalyst, the catalyst may be calcined in air or an inert gas such as nitrogen prior to use, and the catalyst is used after it is calcined in air preferably at 250 to 800° C., more preferably 350 to 600° C., still more preferably 450 to 550° C.

The shape of the catalyst composition of the present invention is not specifically restricted, and a powdery or massive catalyst composition may be used as it is or may be used after it is molded into an arbitrary shape. Examples of shapes of molded catalysts include cylindrical shape, spherical shape, granular shape, ring shape, extruded shape, round granular shape and honeycomb shape. These shapes can be formed by publicly known arbitrary methods respectively suitable for them. The size of the catalyst can be arbitrarily selected from such a range as accords with the size of the reactor. For these molded products, a binder can be used when needed. For example, an inorganic solid having high heat resistance, particularly an oxide carrier, is used as the binder. Specific examples thereof include silica, alumina, zirconia, titania and magnesia. Of these, silica and alumina are preferable, and silica is more preferable. The amount of the binder is preferably 5 to 70% by weight, more preferably 10 to 50% by weight, based on the weight of the catalyst.

[Process for Producing Aromatic Hydrocarbon]

The process for producing an aromatic hydrocarbon of the present invention is a process comprising contacting a raw material gas containing at least one hydrocarbon with the catalyst composition.

The hydrocarbon may be any of a straight-chain hydrocarbon, a hydrocarbon having a branched chain and a hydrocarbon having a ring structure in at least a part of it, as long as it is a hydrocarbon of 1 to 8 carbon atoms. An aliphatic hydrocarbon of 1 to 6 carbon atoms is preferable, and an aliphatic hydrocarbon of 1 to 4 carbon atoms is more preferable. The raw material gas has only to be a gas at least a part of which is a hydrocarbon, and it may be a gas having been diluted with an inert gas.

<Reaction Conditions and Reaction Device>

The reaction temperature (catalyst layer temperature) is 300 to 950° C. An arbitrary temperature in the above range is adopted according to the hydrocarbon used as the raw material gas. For example, when methane is mainly used as the hydrocarbon, the reaction temperature is preferably 600 to 900° C., more preferably 650 to 850° C.

The reaction may be carried out under normal pressure, under increased pressure or under reduced pressure. The reaction pressure is usually 0.0 to 0.8 MPa (megapascal), preferably 0.1 to 0.3 MPa, in terms of an absolute pressure.

As the type of the reactor, any of various types, such as fixed bed type, fluidized bed type, moving bed type, transport bed type, circulating fluidized bed type and combinations thereof, is used. Further, publicly known process techniques, such as a process of recovering/reusing at least a part of an unreacted raw material and a process of membrane-separating hydrogen or the like produced as a by-product, may be combined.

In the present invention, a treatment for activating the catalyst may be carried out prior to the reaction. Specifically, a stream containing one or more gases selected from hydrocarbons of 1 to 8 carbon atoms and hydrogen gas is pre-contacted with the catalyst at a temperature lower than the reaction temperature.

[Regeneration of Catalyst]

The production process of the present invention may comprise a catalyst regeneration step of heating the catalyst in an oxygen-containing atmosphere, and by selecting optimum regeneration conditions, a carbonaceous substance deposited during the reaction can be efficiently removed. Specifically, the catalyst regeneration step is carried out by contacting a mixed gas comprising oxygen and an inert gas (called "regeneration gas" for short hereinafter) with the catalyst. The oxygen concentration in the regeneration gas is not less than 0.1% by volume, preferably not less than 1% by volume but not more than 50% by volume, more preferably not less than 1% by volume but not more than 25% by volume. The oxygen concentration may be kept constant throughout this treatment step, or may be changed stepwise or continuously.

The regeneration temperature (catalyst layer temperature) is usually 350 to 700° C., preferably 400 to 700° C., particularly preferably 600 to 700° C. The catalyst regeneration may be carried out by cooling the catalyst down to the desired temperature from the reaction temperature in an arbitrary inert gas atmosphere after the reaction and then changing the gas to a regeneration gas, or may be carried out by cooling the catalyst down to a low temperature temporarily in an inert gas atmosphere, changing the gas to a regeneration gas and then heating the catalyst up to the desired temperature in a regeneration gas atmosphere. Further, the regeneration treatment may be carried out at a temperature nearly equal to the reaction temperature without cooling the catalyst.

The catalyst regeneration time is 10 minutes to 6 hours, desirably 30 minutes to 1 hour. If this treatment time is excessively short, removal of the deposited carbonaceous substance is incomplete and recovery of activity is insufficient in some cases. On the other hand, if the treatment time is excessively long, the ratio of the regeneration step to the reaction step is high, and lowering of productivity of the process is sometimes brought about. Although the catalyst regeneration may be carried out under normal pressure, under increased pressure or under reduced pressure, the regeneration pressure is usually about 0 to 0.9 MPa, preferably 0.1 to 0.5 MPa, in terms of an absolute pressure.

The present invention is further described with reference to the following examples, but it should be construed that the present invention is in no way limited to those examples.

EXAMPLES

In an X-ray diffraction analysis, a powder X-ray diffractometer MultiFlex 2 kw (Rigaku Corporation) was used, in a Raman spectroscopy, a Microscopic Raman System JRS-SYSTEM 2000 (RENISHAW) was used, and in a weight variation analysis of a catalyst, a differential thermogravimetric analyzer DTG-60H (Shimadzu Corporation) was used.

Catalyst Preparation Example 1

Cerium nitrate ($Ce(NO_3)_3 \cdot 6H_2O$, manufactured by Sigma-Aldrich Corporation) was dissolved in ion-exchanged water. The amount of cerium supported was controlled so that the amount thereof based on the whole catalyst might become 10% by weight after the catalyst preparation (the amount of molybdenum after the catalyst preparation was controlled to 12% by weight based on the whole catalyst). In the solution, 10 g of ammonium type ZSM-5 zeolite (manufactured by Zeolyst International) having a silica/alumina ratio of 30 was suspended. The suspension was stirred for a while and then dried at 120° C. Thereafter, in ion-exchanged water in which ammonium heptamolybdate ($(NH_4)_6Mo_7O_{24} \cdot 4H_2O$, manufactured by Wako Pure Chemical Industries, Ltd.) had been dissolved, the cerium-containing zeolite was suspended. The amount of molybdenum was controlled so that the amount thereof based on the whole catalyst might become 12% by weight after the catalyst preparation (Ce/Mo molar ratio=0.57). The resulting suspension was stirred for a while, then dried at 120° C. and calcined at 500° C. to prepare a catalyst composition 1.

Subsequently, a weight variation as a measure of the amount of molybdenum sublimated during the heating of the catalyst composition 1 was measured using a differential thermogravimetric analyzer, and as a result, a weight reduction of 0.4% by weight was observed. Specifically, the measurement of a weight variation was carried out in the following manner. A sample cup was filled with 0.01 g of the catalyst composition 1, and in the course of temperature increase up to 900° C. in a stream of air, the weight of the catalyst was normalized such that the amount of the catalyst at 650° C. was 100%, and a weight variation of the catalyst at 650° C. or higher was determined. Therefore, the relative weight reduction ratio was 2.4%.

Catalyst Preparation Example 2

Using cerium nitrate in such an amount that the amount of cerium supported might become 5% by weight (Ce/Mo molar ratio=0.29) based on the whole catalyst after the catalyst preparation, a catalyst composition 2 was prepared by the same procedure as in Catalyst Preparation Example 1. The amount of molybdenum supported was controlled so that the amount thereof based on the whole catalyst might become 12% by weight after the catalyst preparation. A weight variation of the catalyst composition 2 was measured in the same manner as described in Catalyst Preparation Example 1, and as a result, a weight reduction of 3.1% by weight was observed. Therefore, the relative weight reduction ratio was 18.5%.

Catalyst Preparation Example 3

Using cerium nitrate in such an amount that the amount of cerium supported might become 2% by weight (Ce/Mo molar ratio=0.11) based on the whole catalyst after the catalyst preparation, a catalyst composition 3 was prepared by the same procedure as in Catalyst Preparation Example 1. The amount of molybdenum supported was controlled so that the amount thereof based on the whole catalyst might become 12% by weight after the catalyst preparation. A weight variation of the catalyst composition 3 was measured in the same manner as described in Catalyst Preparation Example 1, and as a result, a weight reduction of 9.2% by weight was observed. Therefore, the relative weight reduction ratio was 54.4%.

Catalyst Preparation Example 4

Using cerium nitrate in such an amount that the amount of cerium supported might become 5% by weight (Ce/Mo molar ratio=0.57) based on the whole catalyst after the catalyst preparation, a catalyst composition 4 was prepared by the same procedure as in Catalyst Preparation Example 1. The amount of molybdenum supported was controlled so that the amount thereof based on the whole catalyst might become 6% by weight after the catalyst preparation. A weight variation of the catalyst composition 4 was measured in the same manner as described in Catalyst Preparation Example 1, and as a result, a weight reduction of 0.4% by weight was observed. Therefore, the relative weight reduction ratio was 4.60.

Catalyst Preparation Example 5

Using cerium nitrate in such an amount that the amount of cerium supported might become 2.5% by weight (Ce/Mo molar ratio=0.57) based on the whole catalyst after the catalyst preparation, a catalyst composition 5 was prepared by the same procedure as in Catalyst Preparation Example 1. The amount of molybdenum supported was controlled so that the amount thereof based on the whole catalyst might become 3% by weight after the catalyst preparation. A weight variation of the catalyst composition 5 was measured in the same manner as described in Catalyst Preparation Example 1, and as a result, weight reduction was not observed in the temperature increase up to 900° C. Therefore, the relative weight reduction ratio was 0.0%.

Catalyst Preparation Example 6

A catalyst composition 6 was prepared by the same procedure as in Catalyst Preparation Example 1, except that praseodymium nitrate ($Pr(NO_3)_3 \cdot 6H_2O$, manufactured by Sigma-Aldrich Corporation) was used instead of cerium nitrate as a precursor of a second metal. The amount of praseodymium supported was controlled so that the amount thereof based on the whole catalyst might become 10% by weight after the catalyst preparation. The amount of molybdenum was controlled so that the amount thereof based on the whole catalyst might become 12% by weight after the catalyst preparation (Pr/Mo molar ratio=0.57). A weight variation of the catalyst composition 6 was measured in the same manner as described in Catalyst Preparation Example 1, and as a result, a weight reduction of 0.1% by weight was observed. Therefore, the relative weight reduction ratio was 0.6%.

Catalyst Preparation Example 7

A catalyst composition 7 was prepared by the same procedure as in Catalyst Preparation Example 1, except that terbium nitrate ($Tb(NO_3)_3 \cdot 5H_2O$, manufactured by Sigma-Aldrich Corporation) was used instead of cerium nitrate as a precursor of a second metal. The amount of terbium supported was controlled so that the amount thereof based on the whole catalyst might become 10% by weight after the catalyst preparation. The amount of molybdenum was controlled so that the amount thereof based on the whole catalyst might become 12% by weight after the catalyst preparation (Tb/Mo molar ratio=0.50). A weight variation of the catalyst composition 7 was measured in the same manner as described in Catalyst Preparation Example 1, and as a result, a weight reduction of 1.7% by weight was observed. Therefore, the relative weight reduction ratio was 10.2%.

Catalyst Preparation Example 8

A catalyst composition 8 was prepared by the same procedure as in Catalyst Preparation Example 1, except that yttrium nitrate $(Y(NO_3)_3 \cdot 6H_2O$, manufactured by Sigma-Aldrich Corporation) was used as a precursor of a second metal. The amount of yttrium supported was controlled so that the amount thereof based on the whole catalyst might become 10% by weight after the catalyst preparation. The amount of molybdenum was controlled so that the amount thereof based on the whole catalyst might become 12% by weight after the catalyst preparation (Y/Mo molar ratio=0.9). A weight variation of the catalyst composition 8 was measured in the same manner as described in Catalyst Preparation Example 1, and as a result, weight reduction was not observed in the temperature increase up to 900° C. Therefore, the relative weight reduction ratio was 0.0%.

Catalyst Preparation Example 9

Ammonium heptamolybdate $((NH_4)_6Mo_7O_{24} \cdot 4H_2O$, manufactured by Wako Pure Chemical Industries, Ltd.) was dissolved in ion-exchanged water. The amount of molybdenum was controlled so that the amount thereof based on the whole catalyst might become 12% by weight after the catalyst preparation. In the solution, 10 g of ammonium type ZSM-5 zeolite (manufactured by Zeolyst International) having a silica/alumina ratio of 30 was suspended. The suspension was stirred for a while, then dried at 120° C. and calcined at 500° C. to prepare a catalyst composition 9. A weight variation of the catalyst composition 9 was measured in the same manner as described in Catalyst Preparation Example 1, and as a result, a weight reduction of 10.5% by weight was observed. Therefore, the relative weight reduction ratio was 61.8%.

Example 1

Using methane as hydrocarbon gas of a raw material and using a fixed bed flow type reactor, catalytic performance was evaluated in the following manner.

<Activation Treatment>

A reaction tube was filled with 0.3 gram of the catalyst composition 1, and the temperature was raised up to 200° C. in a stream of helium. Thereafter, a mixed gas of methane and hydrogen (methane/hydrogen molar ratio=1/10) was passed through, and the temperature was raised up to 700° C. The temperature was maintained at 700° C. for 80 minutes.

<Reaction Step>

After the activation step, the gas was changed to methane (7.5 mL/min) which was a raw material gas, and the reaction was initiated at 700° C. and under normal pressure. The reactor outlet gas was directly introduced into a gas chromatograph (manufactured by Shimadzu Corporation, GC2014) and analyzed.

<Catalyst Regeneration Step>

After the above reaction step of 18.5 hours, the catalyst regeneration step was carried out in the following manner. The catalyst was cooled down to room temperature in a stream of helium and then heated up to 600° C. Air was passed through at 600° C., and the temperature was maintained at 600° C. for 1 hour. Thereafter, the catalyst was cooled down to room temperature again in a stream of helium. After the same activation treatment step as above was carried out, the catalytic activity after the regeneration was evaluated by the same procedure as in the above reaction step.

The benzene yield (in terms of carbon) was determined by the following formula (1). The relative activity of the catalyst having been subjected to the regeneration step was determined by the following formula (2).

[Math. 1]

$$\text{Benzene yield (\%)} = \frac{(\text{Benzene production (mol)}) \times 6}{(\text{Methane feed (mol)})} \times 100 \quad \text{(Formula 1)}$$

$$\text{Relative activity (\%)} = \frac{\left(\begin{array}{c}\text{Total benzene production based on 18.5 hrs}\\ \text{with regenerated catalyst (mol)}\end{array}\right)}{\left(\begin{array}{c}\text{Total benzene production based on 18.5 hrs}\\ \text{with fresh catalyst (mol)}\end{array}\right)} \times 100 \quad \text{(Formula 2)}$$

A benzene maximum yield exhibited by the catalyst composition 1 in the reaction step, a benzene maximum yield exhibited by the catalyst composition 1 after the regeneration treatment and a relative activity are set forth in Table 1.

A change of the benzene yield with time given when the fresh catalyst was used and a change of the benzene yield with time given when the regenerated catalyst obtained in the regeneration step was subjected to an activation step and a reaction step again are shown in FIG. 1. A maximum value of the benzene yield in the case where the reaction step was carried out using the fresh catalyst or the regenerated catalyst (described as "first reaction" or "second reaction" in FIG. 1) was read out from FIG. 1 and taken as a benzene maximum yield. The relative activity defined by the above formula 2 was 96%.

These results indicate that durability of the catalyst in the catalyst regeneration step under the high-temperature conditions was improved by adding cerium in a specific amount, and it can be seen that even if the reaction step and the catalyst regeneration step are repeated, catalyst deterioration is inhibited over a long period of time.

Comparative Example 1

Catalytic performance was evaluated in the same manner as in Example 1, except that the catalyst composition 9 was used as a catalyst. The results are set forth in Table 1. Further, a change of a benzene yield with time is shown in FIG. 2.

The activity of the fresh catalyst was nearly equal to that in the case of Example 1, but the relative activity given when the reaction step was carried out again after the regeneration step and the activation step was lowered down to 83%.

From these results, it is apparent that in the case of the catalyst composition containing no cerium, durability of the catalyst was low, and catalyst deterioration was brought about in the catalyst regeneration step under the high-temperature conditions.

TABLE 1

| Catalyst | | Benzene maximum yield | Relative activity |
|---|---|---|---|
| Ex. 1 | catalyst composition 1 | 7.00% | 96% |
| | catalyst composition 1 (after regeneration) | 7.10% | |
| Comp. Ex. 1 | catalyst composition 9 | 7.50% | 83% |
| | catalyst composition 9 (after regeneration) | 6.80% | |

Example 2

Performance evaluation of the catalyst compositions 1, 3, 4, 5 and 9 was carried out in the same manner as in Example 1, except that in the catalyst regeneration step, the catalyst was directly cooled down to 600° C. in a stream of helium after the reaction step, then air was passed through, the temperature was maintained at 600° C. for 1 hour, and the activation step, the reaction step and the catalyst regeneration step were repeated 4 to 6 times. The results are shown in FIG. 3 and Table 2.

From these results, it can be seen that catalyst deterioration of the catalyst compositions of the present invention due to repetition of the reaction step and the catalyst regeneration step was inhibited.

TABLE 2

| | Maximum benzene yield in each reaction cycle/% | | | | | |
|---|---|---|---|---|---|---|
| | 1st | 2nd | 3rd | 4th | 5th | 6th |
| Catalyst composition 1 | 7.0 | 7.1 | 7.0 | 6.7 | 6.5 | 6.1 |
| Catalyst composition 3 | 7.3 | 6.6 | 5.6 | 4.3 | | |
| Catalyst composition 4 | 6.8 | 7.1 | 7.0 | 6.7 | 6.6 | |
| Catalyst composition 5 | 4.5 | 5.1 | 4.8 | 4.4 | 4.0 | |
| Catalyst composition 9 (Comp. Ex.) | 7.2 | 5.8 | 4.7 | 3.5 | 2.6 | 1.9 |

Example 3

Catalyst performance was evaluated in the same manner as in Example 2, except that the catalyst compositions 1, 6, 7, 8 and 9 and the catalyst composition 8a obtained by heat-treating the catalyst composition 8 at 600° C. for 168 hours in an air atmosphere were used as catalysts. The results are shown in FIG. 4 and Table 3.

From these results, it can be seen that catalyst deterioration of the catalyst compositions of the present invention due to repetition of the reaction step and the catalyst regeneration step was inhibited.

TABLE 3

| | Maximum benzene yield in each reaction cycle/% | | | | | |
|---|---|---|---|---|---|---|
| | 1st | 2nd | 3rd | 4th | 5th | 6th |
| Catalyst composition 1 | 7.0 | 7.1 | 7.0 | 6.7 | 6.5 | 6.1 |
| Catalyst composition 6 | 6.5 | 7.3 | 7.2 | 7.0 | 6.7 | 6.5 |
| Catalyst composition 7 | 6.2 | 7.1 | 7.0 | 6.8 | 6.5 | 6.1 |
| Catalyst composition 8 | 1.2 | 4.4 | 4.3 | 3.9 | 3.9 | |
| Catalyst composition 8a | 5.4 | 5.7 | 5.6 | 5.6 | 5.5 | 5.4 |
| Catalyst composition 9 (Comp. Ex.) | 7.2 | 5.8 | 4.7 | 3.5 | 2.6 | 1.9 |

In FIG. 5a, Raman spectroscopy spectra of the catalyst compositions 1, 4, 5 and 9 are shown, and in FIG. 5b, an enlarged view of the 800 to 1100 $cm^{-1}$ portion in FIG. 5a is shown. The Y/X values obtained from the spectra are set forth in Table 4.

TABLE 4

| | $cm^{-1}$ | Catalyst composition 1 | Catalyst composition 4 | Catalyst composition 5 | Catalyst composition 9 |
|---|---|---|---|---|---|
| X | 900-970 | 28763.21 | 11996.26 | 3160.44 | 2273.96 |
| Y | 980-1020 | 10486.51 | 5754.96 | 1307.24 | 54568.05 |
| Y/X | | 0.36 | 0.48 | 0.41 | 24.00 |

As previously described, it is considered that if the Y/X ratio is small, a layer of a metal oxide containing molybdenum and the second metal has been formed. The compositions 1, 4 and 5 each had a Y/X ratio of 0.5 or less and had a value in a preferred range. On the other hand, the catalyst composition 9 which was a comparative example had an extremely large Y/X ratio, and it indicates that a composite oxide was not formed.

Measured data of the XRD measurement are shown in FIG. 5c, and as a crystalline structure of a publicly known molybdenum-containing oxide layer, JCPDS number 30-0303 is shown in FIG. 5d. It can be confirmed that in the measured data, at least one peak corresponding to the JCPDS number 30-0303 is shown, and it is indicated that the catalyst composition has a crystalline structure of a molybdenum-containing composite oxide layer.

INDUSTRIAL APPLICABILITY

The catalyst composition of the present invention can be applied to a process for producing an aromatic hydrocarbon from a lower hydrocarbon such as methane.

The invention claimed is:

1. A catalyst composition for producing an aromatic hydrocarbon by contacting at least one hydrocarbon with the catalyst composition, comprising molybdenum, a second metal that is not molybdenum, and a crystalline metallosilicate, wherein the content of molybdenum is 1 to 20% by weight in terms of a molybdenum atom and the content of the second metal is 5 to 20% by weight in terms of a metal atom, wherein the second metal is at least one metal selected from the group consisting of Sc, Ce, Pr, Pm, Eu, Gd, Tb, Dy, Ho, Er, Tm, Yb, and Lu, wherein the ratio (y/x) of the content (y mol) of the second metal atom to the content (x mol) of the molybdenum atom is 0.4 to 5, and wherein a relative weight reduction ratio (C) defined by the following formula is 60% or less;

$$C = 100 A/B;$$

wherein,

A is a weight variation in terms of %, which is defined as a deviation in weight at a temperature of 900° C. based on a weight measured at a temperature of 650° C. wherein the measurement is conducted by heating the catalyst composition with a differential thermogravimetric analyzer at a temperature increase rate of 5° C. per minute from a room temperature to 900° C. in air atmosphere, wherein the weight of the catalyst composition is normalized such that the weight of the catalyst composition at 650° C. is 100%; and, B is molybdenum oxide content in terms of wt % to the total wt % of a catalyst composition (100 wt %) in which both of the molybdenum and the second metal are in the form of oxides.

2. The catalyst composition according to claim 1, wherein in an X-ray diffraction analysis of said catalyst composition, at least one peak attributed to a composite oxide phase of molybdenum and the second metal, which is different from a peak attributed to a single phase of each of molybdenum oxide and the second metal oxide, is observed.

3. The catalyst composition according to claim 1, wherein in a Raman spectroscopy the ratio (Y/X) of a maximum peak strength of the spectrum in the range of 980 to 1020 $cm^{-1}$ (Y) to a maximum peak strength of the spectrum in the range of 900 to 970 $cm^{-1}$ (X) is 0.8 or lower.

4. The catalyst composition according to claim 1, wherein the second metal is at least one metal selected from the group consisting of Ce, Pr, and Tb.

5. The catalyst composition according to claim 1, wherein the crystalline metallosilicate has a pore having a diameter of 4 to 9 Å.

6. The catalyst composition according to claim 5, wherein the crystalline metallosilicate has a MFI-type or a MWW-type crystalline structure.

7. The catalyst composition according to claim 6, wherein the crystalline metallosilicate is aluminosilicate.

8. The catalyst composition according to claim 1, wherein the relative weight reduction ratio (C) is 30% or less.

9. A process for producing an aromatic hydrocarbon comprising a step of contacting at least one hydrocarbon with the catalyst composition according to claim 1.

10. The process for producing an aromatic hydrocarbon according to claim 9, wherein the hydrocarbon is an aliphatic hydrocarbon having 1 to 6 carbon atoms.

11. The process for producing an aromatic hydrocarbon according to claim 9, which further comprises a regeneration step of heating the catalyst under an oxygen-containing atmosphere to a temperature of 400° C. or higher.

* * * * *